United States Patent [19]

O'Brien

[11] Patent Number: 5,527,183

[45] Date of Patent: Jun. 18, 1996

[54] ENDOSSEOUS IMPLANT SYSTEM

[75] Inventor: Gary O'Brien, Glendale, Calif.

[73] Assignee: Collaborative Enterprises, Inc., Glendale, Calif.

[21] Appl. No.: 288,278

[22] Filed: Aug. 9, 1994

Related U.S. Application Data

[63] Continuation-in-part of Ser. No. 108,869, Aug. 18, 1993, Pat. No. 5,435,723.

[51] Int. Cl.$^6$ ...................................................... A61C 8/00
[52] U.S. Cl. .......................................... 433/174; 433/173
[58] Field of Search ................................... 433/172, 173, 433/174, 175, 176

[56] References Cited

U.S. PATENT DOCUMENTS 711,324  10/1902  Lacy .
866,304   9/1907  Roach .

(List continued on next page.)

FOREIGN PATENT DOCUMENTS

| 0073177 | 8/1982 | European Pat. Off. . |
| 604674 | 7/1975 | Germany . |
| 2834890A1 | 8/1978 | Germany . |
| 3027138A1 | 7/1980 | Germany . |
| 3423752A1 | 6/1984 | Germany . |
| 9898819 | 12/1969 | Japan . |

(List continued on next page.)

OTHER PUBLICATIONS

"The Journal of Prosthetic Dentistry," published by Mosby Co., vol. 50, No. 1.
"Osseointegrated Titanium Implants: Requirements for Ensuring a Long-Lasting, Direct Bone-to-Implant Anchorage in Man," by Albrektsson et al., 1981.
"Osseointegrated Impants in the Treatment of the Edentulous Jaw: Experience from a 10-year Period," by Branemark et al., 1977.
"Ampfungsraum Optimiert: PITT–ISIS BIO–OSS," by Prof. Y. N. Ismail, D. M. D., Ph.D.

Primary Examiner—Cary E. O'Connor
Attorney, Agent, or Firm—Morton J. Rosenberg; David I. Klein

[57] ABSTRACT

An endosseous implant body for affixing an orthopedic prosthesis into bone is provided. The implant body generally has at least four segments disposed proximate to a coronal end of the implant body. Each segment consists of a frustro-conical compression moiety and a frustro-conical tension moiety. The angles of incidence and the surface areas of the compression moieties are chosen so that, when the body is implanted into bone and a lateral force is applied to the coronal end of the body, that portion of the lateral force which is exerted by the compression moiety of each segment against the surrounding bone is greater than that portion of the lateral force which is exerted by the compression moiety of an adjacent segment disposed more proximate to the coronal end. Likewise, the angles of incidence and the surface areas of the tension moieties are chosen so that, when the body is implanted into bone and a lateral force is applied to the coronal end of the body, that portion of the lateral force which is exerted by the tension moiety of each segment against the surrounding bone is less than that portion of the lateral force which is exerted by the tension moiety of an adjacent segment disposed more proximate to the coronal end. The implant body of the invention has been found to produce a stable implant sight for orthopedic prostheses, especially dental prostheses. The design of the implant body results in a much more even distribution of occlusal forces to the prosthesis, thereby minimizing degradation of the implant sight over time. Additionally, the invention employs a new prosthetic connection in which one or both components (the body and prosthesis attachment structure) contain a Mores taper which locks the attachment structure to the body of the implant when properly attached. The assembly may also be designated with multiple orientations or only one orientation circumferentially.

21 Claims, 12 Drawing Sheets

U.S. PATENT DOCUMENTS

| | | | |
|---|---|---|---|
| 2,112,007 | 3/1938 | Adams . | |
| 2,347,567 | 4/1944 | Kresse . | |
| 2,609,604 | 9/1952 | Sprague . | |
| 2,774,141 | 12/1956 | Quinn . | |
| 3,435,526 | 4/1969 | Brancato | 433/174 |
| 3,499,222 | 3/1970 | Linkow et al. . | |
| 3,729,825 | 5/1973 | Linkow et al. . | |
| 3,732,621 | 5/1973 | Bostrom . | |
| 3,787,975 | 1/1974 | Zuest . | |
| 3,849,887 | 11/1974 | Brainin . | |
| 3,849,888 | 11/1974 | Linkow . | |
| 3,919,774 | 11/1975 | Fishman . | |
| 4,016,651 | 4/1977 | Kawahara et al. . | |
| 4,053,982 | 10/1977 | Weissman . | |
| 4,109,383 | 8/1978 | Reed et al. . | |
| 4,177,562 | 12/1979 | Miller et al. | 433/174 |
| 4,180,910 | 1/1980 | Straumann et al. | 433/173 |
| 4,187,609 | 2/1980 | Edelman | 433/176 |
| 4,195,367 | 4/1980 | Kraus | 433/173 |
| 4,204,321 | 5/1980 | Scott | 433/174 |
| 4,259,072 | 3/1981 | Hirbayashi et al. | 433/173 |
| 4,290,755 | 9/1981 | Scott | 433/173 |
| 4,302,188 | 11/1981 | Driskell | 433/173 |
| 4,324,550 | 4/1982 | Reuther et al. | 433/174 |
| 4,334,865 | 6/1982 | Borle | 433/221 |
| 4,359,318 | 11/1982 | Gittleman | 433/173 |
| 4,416,629 | 11/1983 | Mozsary et al. | 433/174 |
| 4,431,416 | 2/1984 | Niznick | 433/174 |
| 4,468,200 | 8/1984 | Munch | 433/174 |
| 4,488,875 | 12/1984 | Niznick | 433/173 |
| 4,552,532 | 11/1985 | Mozsary | 433/173 |
| 4,573,922 | 3/1986 | Bello | 433/176 |
| 4,645,453 | 2/1987 | Niznick | 433/173 |
| 4,661,066 | 4/1987 | Linkow et al. | 433/176 |
| 4,668,191 | 5/1987 | Plischka | 433/174 |
| 4,713,004 | 12/1987 | Linkow et al. | 433/174 |
| 4,780,080 | 10/1988 | Haris | 433/173 |
| 4,842,518 | 6/1989 | Linkow et al. | 433/174 |
| 4,856,994 | 8/1989 | Lazzara et al. | 433/174 |
| 4,904,187 | 2/1990 | Zingheim | 433/173 |
| 4,908,030 | 3/1990 | Linkow et al. | 623/16 |
| 4,915,628 | 4/1990 | Linkow et al. | 433/173 |
| 4,932,868 | 6/1990 | Linkow et al. | 433/174 |
| 4,944,754 | 7/1990 | Linkow et al. | 623/16 |
| 4,960,381 | 10/1990 | Niznick | 433/174 |
| 4,995,810 | 2/1991 | Soderberg | 433/174 |
| 5,030,095 | 7/1991 | Niznick | 433/173 |
| 5,061,181 | 10/1991 | Niznick | 433/174 |
| 5,071,350 | 12/1991 | Niznick | 433/173 |
| 5,076,788 | 12/1991 | Niznick | 433/173 |
| 5,078,607 | 1/1992 | Niznick | 433/174 |
| 5,116,225 | 5/1992 | Riera | 433/174 |
| 5,178,539 | 1/1993 | Peltier et al. | 433/173 |
| 5,180,303 | 1/1993 | Hornburg et al. | 433/173 |
| 5,194,000 | 3/1993 | Dury | 433/173 |
| 5,195,891 | 3/1993 | Sulc | 433/173 |
| 5,195,892 | 3/1993 | Gersberg | 433/174 |
| 5,197,881 | 3/1993 | Chalifoux | 433/173 |
| 5,199,873 | 4/1993 | Schulte et al. | 433/174 |
| 5,205,745 | 4/1993 | Kamiya et al. | 433/173 |
| 5,205,746 | 4/1993 | Chanavaz | 433/174 |
| 5,209,659 | 5/1993 | Friedman et al. | 433/173 |
| 5,209,666 | 5/1993 | Baltour et al. | 433/173 |
| 5,221,204 | 6/1993 | Kruger et al. | 433/173 |
| 5,232,364 | 8/1993 | Rosen | 433/173 |
| 5,238,405 | 8/1993 | Marlin | 433/173 |
| 5,242,303 | 9/1993 | De Buck | 433/173 |
| 5,246,369 | 9/1993 | Poulmair | 433/173 |
| 5,246,370 | 9/1993 | Coatoam | 433/173 |
| 5,254,005 | 10/1993 | Zuest | 433/173 |
| 5,259,759 | 11/1993 | Jorneus | 433/173 |
| 5,269,685 | 12/1993 | Jorneus | 433/174 |
| 5,269,686 | 12/1993 | James | 433/174 |
| 5,286,196 | 2/1994 | Brajnovic et al. | 433/173 |
| 5,292,252 | 3/1994 | Nickerson et al. | 433/173 |
| 5,302,126 | 4/1994 | Wimmer et al. | 433/173 |
| 5,302,127 | 4/1994 | Crisio, Jr. | 433/173 |
| 5,302,128 | 4/1994 | Suga | 433/176 |

FOREIGN PATENT DOCUMENTS

| | | | |
|---|---|---|---|
| 48438 | 12/1969 | Japan . | |
| 660342 | 11/1949 | United Kingdom . | |
| 757487 | 1/1953 | United Kingdom . | |
| 968672 | 1/1961 | United Kingdom . | |
| 937944 | 7/1962 | United Kingdom . | |
| 1203093 | 9/1967 | United Kingdom . | |
| 1291470 | 4/1969 | United Kingdom . | |
| 1352188 | 4/1971 | United Kingdom . | |
| 1544784 | 4/1977 | United Kingdom . | |
| 1565178 | 2/1978 | United Kingdom . | |
| 2063680 | 11/1980 | United Kingdom . | |
| 2112683 | 9/1982 | United Kingdom . | |
| 2117641 | 2/1983 | United Kingdom . | |
| 2199502 | 7/1988 | United Kingdom . | |
| 85/04321 | 10/1985 | WIPO . | |
| 86/01705 | 3/1986 | WIPO . | |
| 91/10410 | 7/1991 | WIPO | 433/173 |

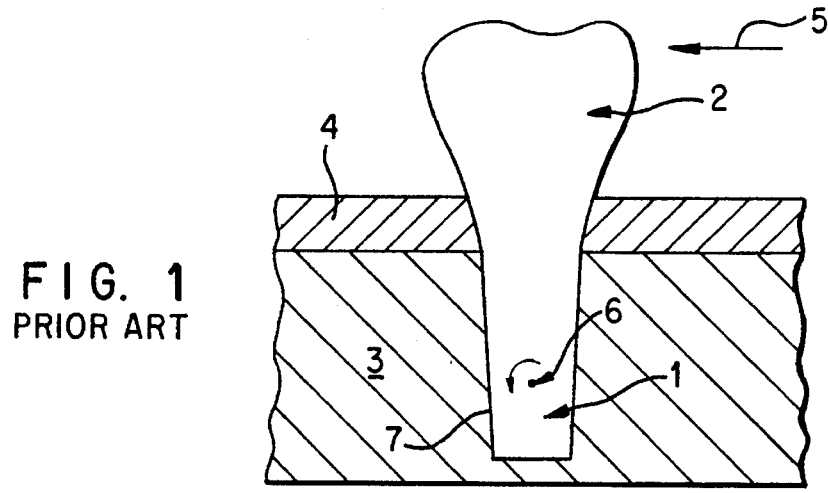
FIG. 1
PRIOR ART
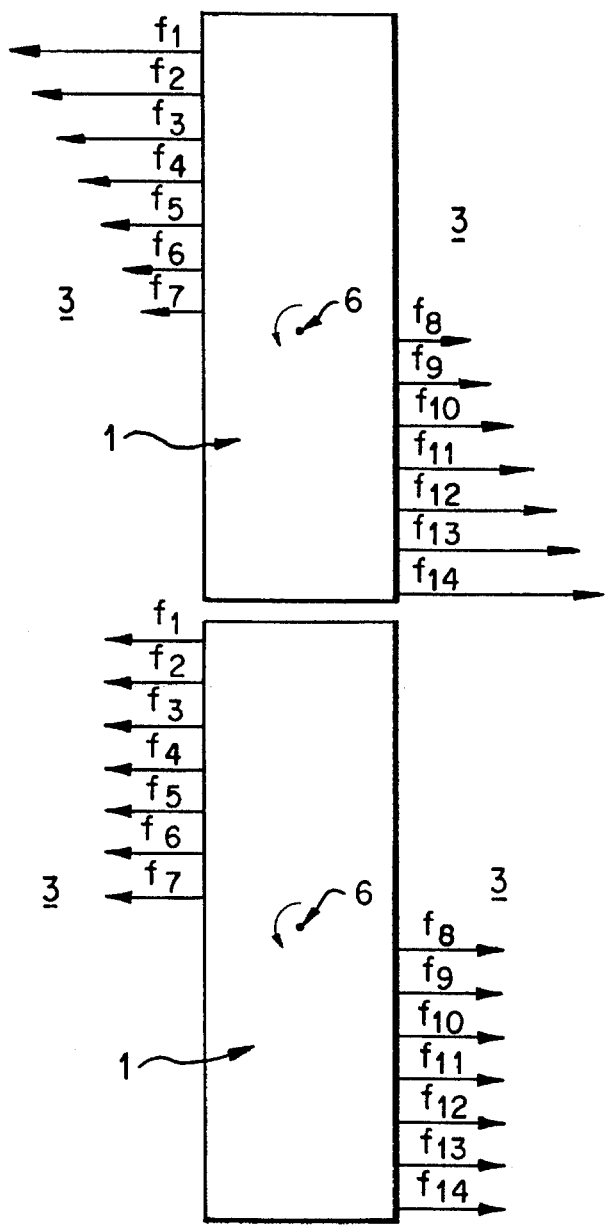
FIG. 2
PRIOR ART
FIG. 3

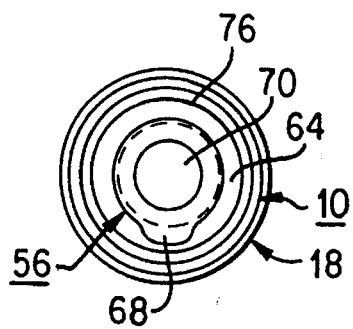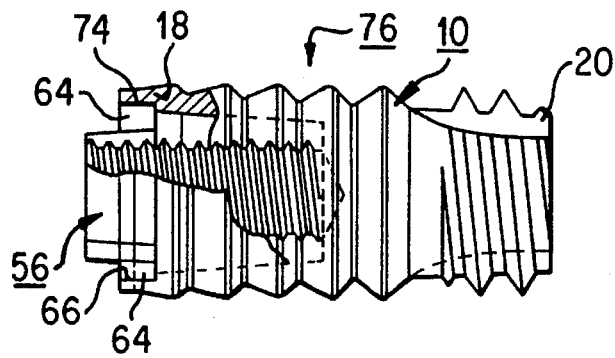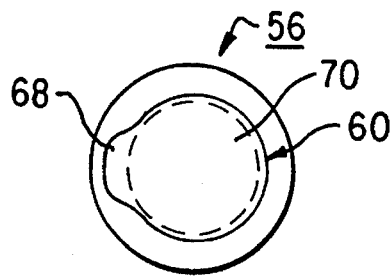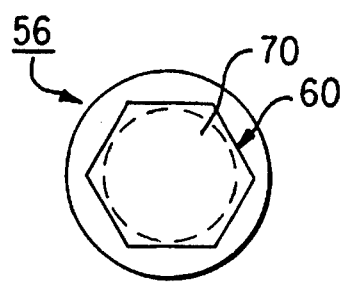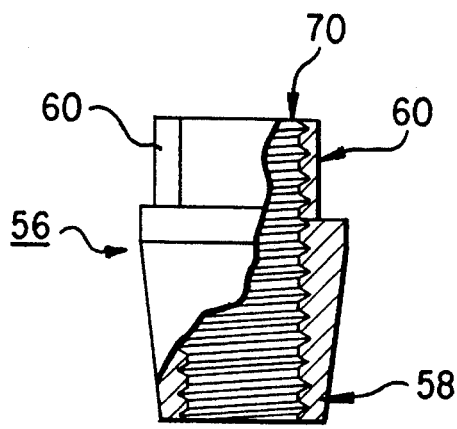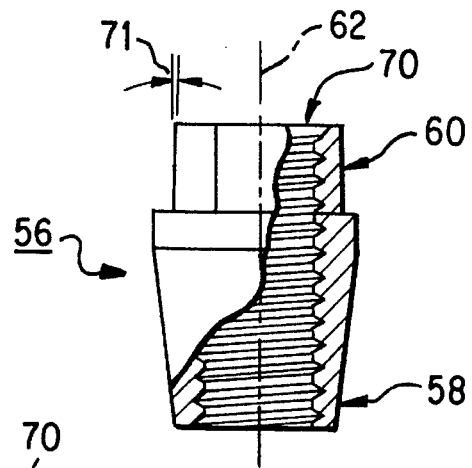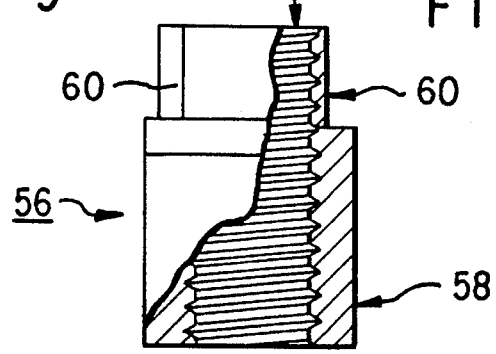

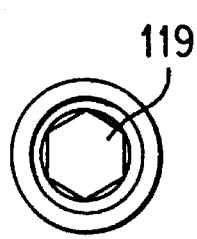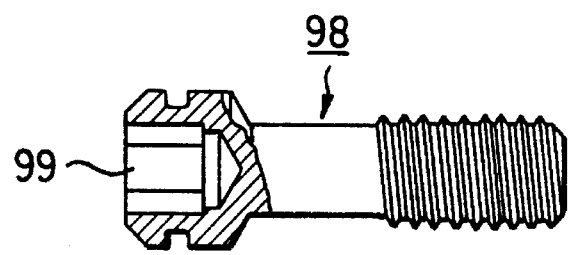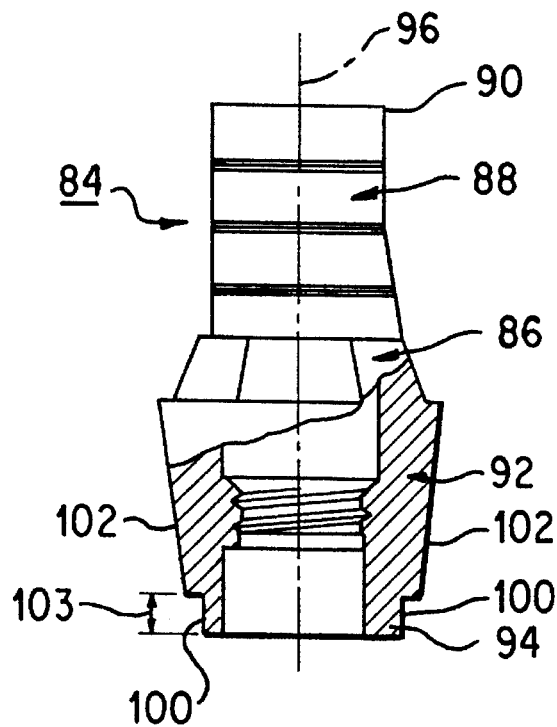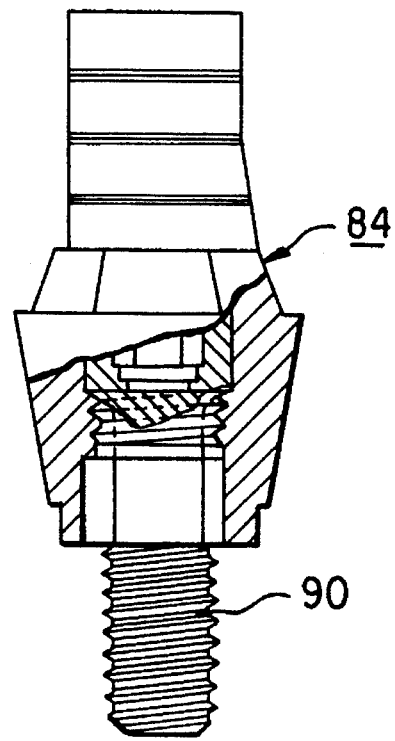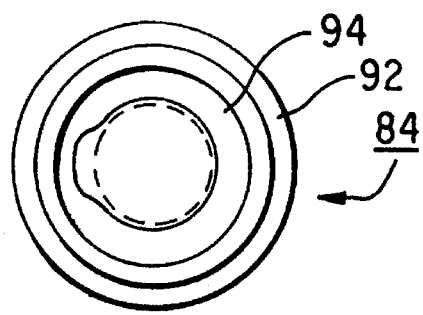

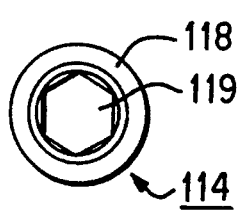
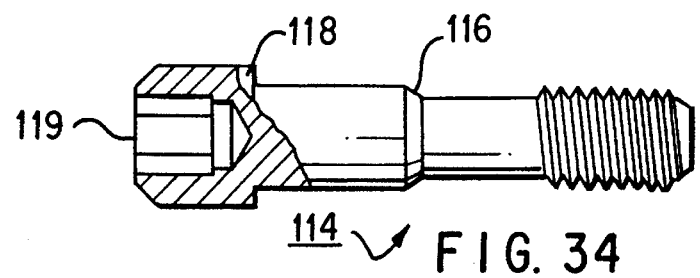
FIG. 35
FIG. 34
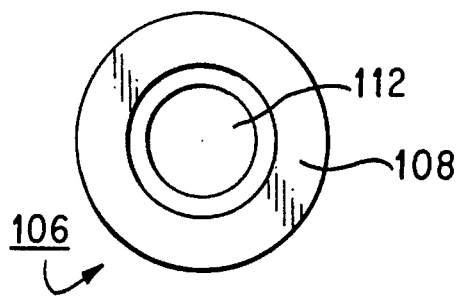
FIG. 33
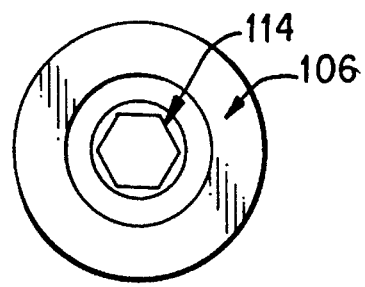
FIG. 30
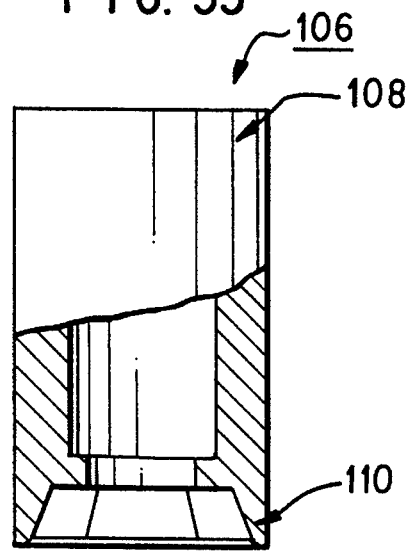
FIG. 31
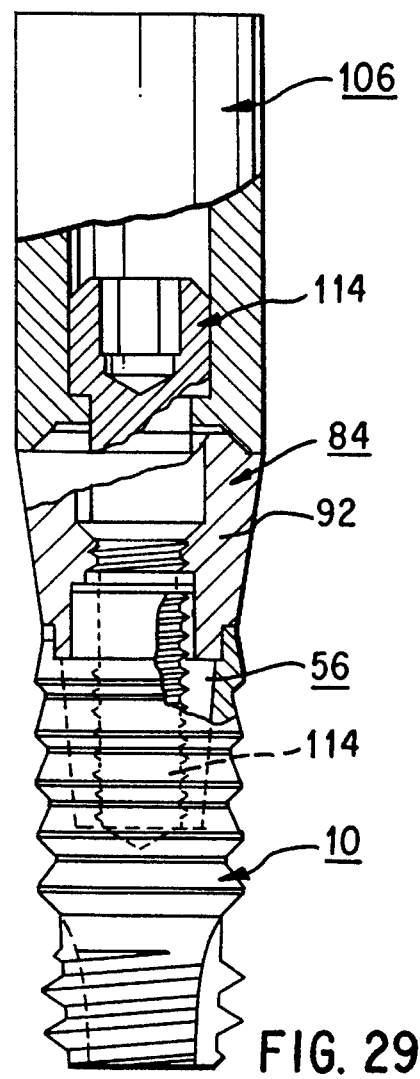
FIG. 29
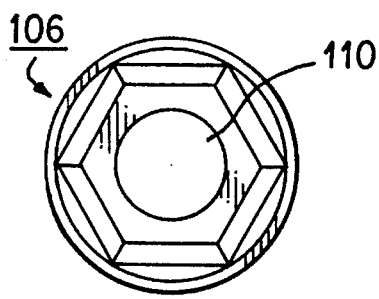
FIG. 32

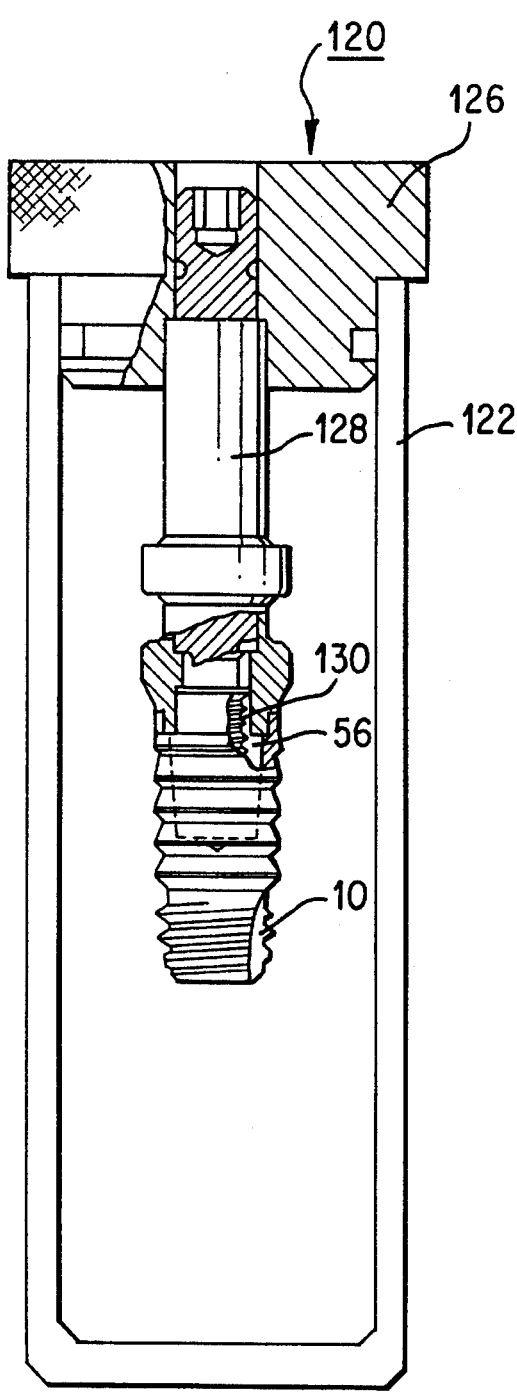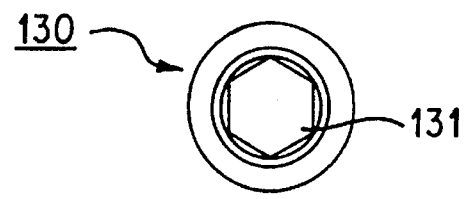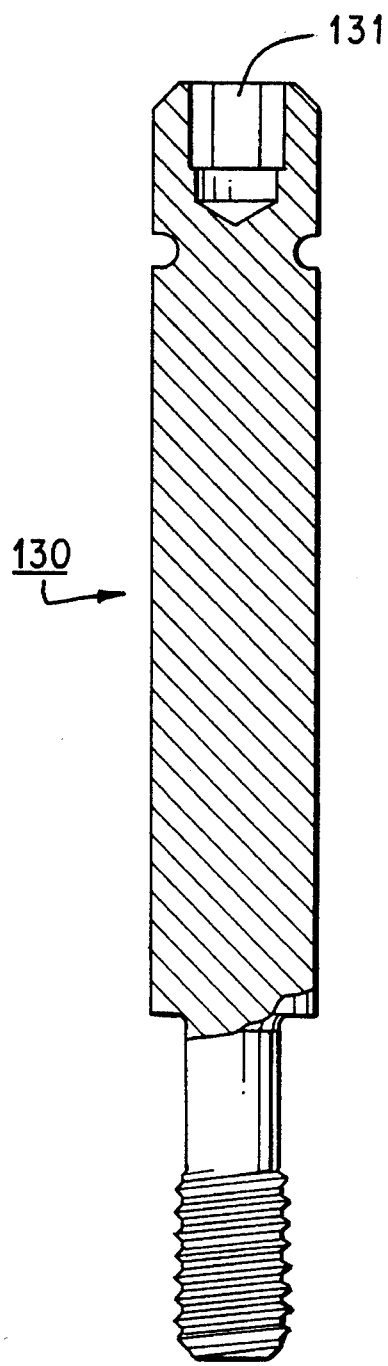
FIG. 36
FIG. 38
FIG. 37

ENDOSSEOUS IMPLANT SYSTEM

RELATED APPLICATIONS

This application is a continuation-in-part of U.S. patent application Ser. No. 08/108,869, filed Aug. 18, 1993, now U.S. Pat. No. 5,435,723.

FIELD OF THE INVENTION

This invention relates generally to artificial orthopedic implant prostheses, and particularly, but not exclusively, to dental implant prostheses.

BACKGROUND OF THE INVENTION

The installation of an orthopedic prosthesis, whether it be a dental prosthesis such as bridge work or other bone implant prosthesis such as an artificial limb, requires affixing the prosthesis to one of the patient's bones. Generally, this is accomplished by first affixing a metallic implant connection member into the connector bone and then affixing the prosthesis to the implant connection member.

A fundamental problem with the installation of orthopedic prostheses is the tendency of the bone installation sight to "wear out" over time. This resorption of bone ("wear out") is characteristically seen after load is introduced. Clinical evidence of this destruction begins at the coronal aspect and moves progressively towards the apical end of the fixture creating a uniform saucerization. The fundamental problem is the inability of prior art implant systems to evenly distribute occlusal loads along the length of the implant connection member. This results in uneven stress to the bone immediately surrounding the implant connection member, and leads to eventual break-down of the implant sight. This problem is particularly acute with respect to dental implants, but it is also a common problem with respect to other orthopedic implants.

Therefore, there is a need for an endosseous implant system wherein the implant member is capable of more evenly distributing occlusal loads along the entire length of the implant connection member.

SUMMARY OF THE INVENTION

The invention satisfies this need. The invention is an endosseous implant body for implantation into bone. The implant body has a coronal end, a distal end and a plurality of segments proximate to the coronal end.

Each segment has a circular cross-section perpendicular to the longitudinal axis of the implant body and comprises a frustro-conical compression moiety and a frustro-conical tension moiety. As used herein, the term "tension moiety" means the coronal-side portion of the segment whose surface area generally faces in the direction of the coronal end of the implant body. Conversely, the term "compression moiety" as used herein means the distal-side portion of the segment whose surface area generally faces towards the distal end of the implant body.

Within each segment, both the compression moiety and the tension moiety have a maximum diameter, a minimum diameter and a substantially flat surface area disposed therebetween at an angle of incidence with respect to the longitudinal axis of the implant body. The angle of incidence is the obtuse angle formed by the intersection of the longitudinal axis of the implant body and a line drawn tangent to the flat surface area of one of the moieties.

The compression moiety is joined "back-to-back" with the tension moiety along each moiety's respective maximum diameter. The minimum diameter of each compression moiety is identical to and is attached to the minimum diameter of a tension moiety of an adjacent segment, if any.

The angles of incidence of all segment moieties and the surface areas of all segment moieties are chosen so that, when the implant body is implanted into bone and a lateral force is applied to the coronal end of the body, that portion of the lateral force which is exerted by the compression moiety of each segment against the surrounding bone is greater than that portion of the lateral force which is exerted by the compression moiety of an adjacent segment disposed more proximate to the coronal end.

Likewise, the angles of incidence and the surface areas of each of the tension moieties are chosen so that, when the body is implanted into bone and a lateral force is applied to the coronal end of the body, that portion of the lateral force which is exerted by the tension moiety of each segment against the surrounding bone is less than that portion of the lateral force which is exerted by the tension moiety of an adjacent segment disposed more proximate to the coronal end.

In one embodiment, the width of each compression moiety surface is greater than the width of the compression moiety surface of an adjacent segment disposed more proximate to the distal end. In this embodiment, the width of each tension moiety surface is generally chosen so as to be greater than the width of the tension moiety surface of an adjacent segment disposed more proximate to the coronal end.

Alternatively, the angle of incidence of each compression moiety surface can be chosen so as to be greater than the angle of incidence of the compression moiety surface of the compression moiety disposed more proximate to the distal end. In this embodiment, the angle of incidence of each compression moiety surface is generally chosen so that the angle of incidence of any one compression moiety surface is greater than the angle of incidence of the compression moiety surface disposed more proximate to the coronal end.

The invention is also a combination of an implant body having a coronal end bore and a plug disposed within the coronal end bore. The plug has a coronal end adapted for attachment to a prosthesis attachment member. The coronal end of the plug has at least one non-circular cross-section so that it attaches to the prosthesis attachment member in one and only one position. The plug may also be in the form of a tapered external hex or spline or slot.

The invention is also an implant delivery system comprising the combination described immediately above and an implanting tool. Such an implant system can be conveniently used to install the implant combination described above.

DESCRIPTION OF DRAWINGS

These and other features, aspects and advantages of the present invention will become better understood with reference to the following description, appended claims and accompanying drawings where:

FIG. 1 is a diagrammatic representation of a lateral force exerted on an endosseous prosthesis implanted into bone;

FIG. 2 is a force diagram showing typical forces imposed upon the endosseous implant of FIG. 1;

FIG. 3 is a force diagram showing ideal forces imposed upon the endosseous implant of FIG. 1;

FIG. 9 is a side view in partial cross-section of a plug having features of the invention;

FIG. 9A is a side view in partial cross-section of an alternative plug which is non-tapered;

FIG. 10 is a coronal view of the plug of FIG. 9;

FIG. 11 is a second embodiment of a plug having features of the invention;

FIG. 12 is a coronal view of the plug of FIG. 11 with the external tapered hex design option;

FIG. 13 is a side view in partial cross-section of an implant combination having features of the invention;

FIG. 14 is a coronal view of the combination shown in FIG. 13;

FIG. 20 is a side view in partial cross-section of an attachment structure having features of the invention;

FIG. 21 is a distal end view of the attachment structure of FIG. 20;

FIG. 22 is a side view in partial cross-section of a screw useful in the attachment of the attachment structure of FIG. 20;

FIG. 23 is a coronal end view of the screw illustrated in FIG. 22;

FIG. 24 is a side view in partial cross-section of a combination of the attachment structure of FIG. 20 and the screw of FIG. 22.

FIG. 29 is a side view in partial cross-section of a combination having features of the invention, including a cover sheath;

FIG. 30 is a coronal end of the combination of FIG. 29;

FIG. 31 is a side view in partial cross-section of a sheath useable in the combination of FIG. 29;

FIG. 32 is a coronal end view of the sheath of FIG. 31;

FIG. 33 is a distal end view of the sheath of FIG. 31;

FIG. 34 is a side view in partial cross-section of a screw useful in the combination of FIG. 29;

FIG. 35 is a coronal end view of the screw of FIG. 34;

FIG. 36 is a side view in partial cross-section of an endosseous implant delivery system having features of the invention;

FIG. 37 is a side view in partial cross-section of a screw useful in the delivery system of FIG. 36;

FIG. 38 is a coronal end view of the screw of FIG. 37;

DETAILED DESCRIPTION OF THE INVENTION

Figure 4:
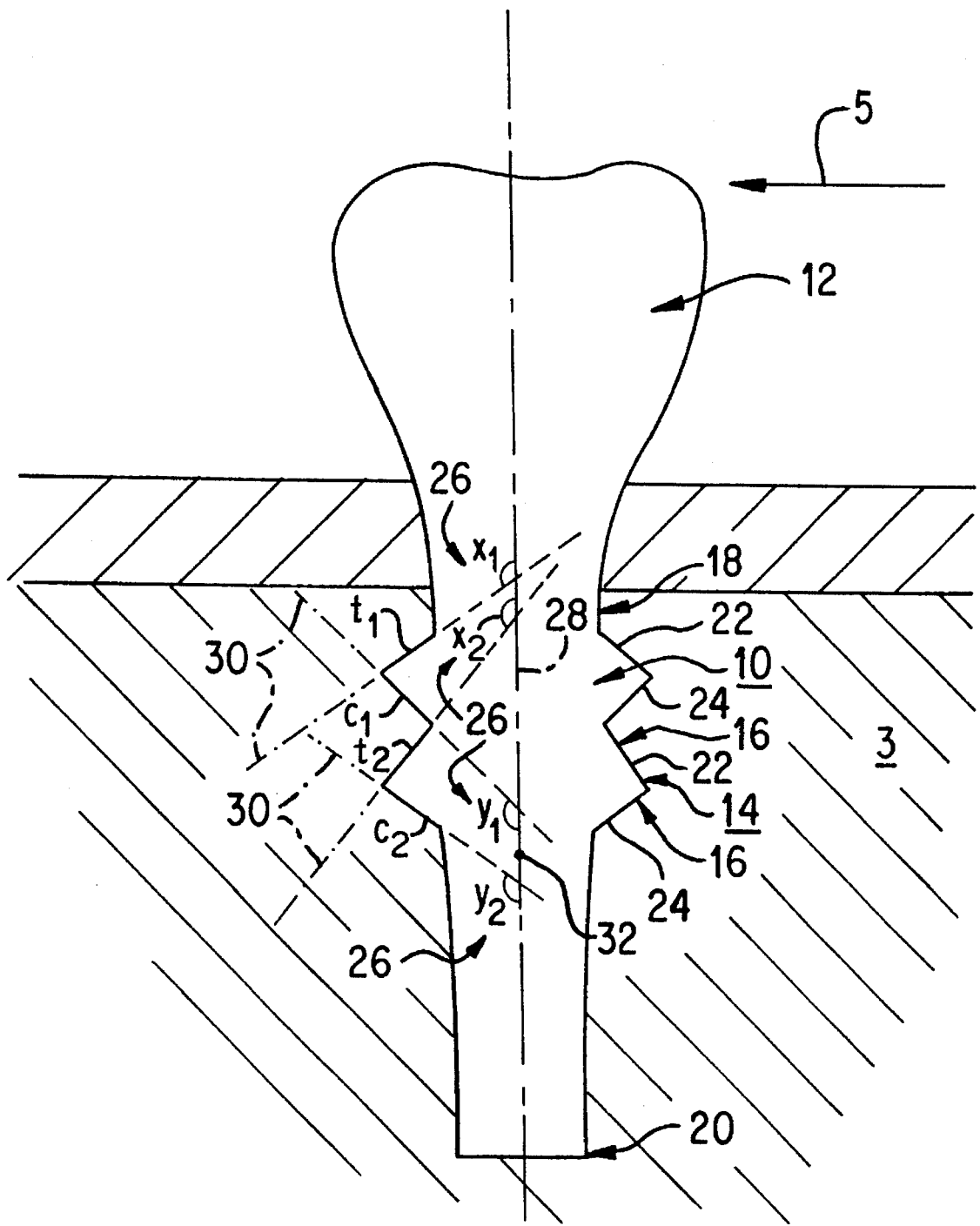
FIG. 4 is a diagrammatic representation of a lateral force exerted on an endosseous prosthesis having features of the invention implanted into bone.

The invention will be described by using specific language with reference to the accompanying illustrated embodiments. Although much of this description is directed to dental implants, it is understood that the scope of the invention includes other orthopedic implants and any modifications or alterations which would be obvious to those skilled in the art.

FIG. 1 illustrates a typical prior art endosseous dental implant body 1 and prosthesis 2 implanted into a patient's jawbone 3 below the gum line 4. When a lateral force 5 is applied to such a typical dental implant 1, that lateral force 5 tends to rotate the implant 1 about a certain point in the implant 1, which will be referred to herein as the "centroid 6." The location of the centroid 6 depends on the design of the implant 1. The lateral force 5 generates stress forces $f_i$ within the jawbone 3 as illustrated by the force diagram shown in FIG. 2. As can be seen from FIG. 2, with prior art implant bodies the stress forces $f_i$ placed upon the adjacent bone 3 furthest from the centroid 6 are much greater than the stress forces placed upon the bone 3 near the centroid 6. The excessive stress forces $f_i$ placed upon the bone 3 adjacent to the implant body 1 furthest from the centroid 6 frequently results in degradation of that bone 3 over time.

What would be ideal would be an endosseous implant body which, when a lateral force is applied to the implant body, would evenly distribute the stress forces $f_i$ applied to the bone adjacent to the implant body. Such an ideal stress force distribution is illustrated in FIG. 3. It is the principal object of the present invention to provide an endosseous implant body which will more closely approximate the stress forces illustrated in FIG. 3 (rather than the stress forces associated with prior art implants, as illustrated in FIG. 2).

The stress force diagram illustrated in FIG. 2 arises typically from an implant body 1 having a substantially cylindrical shape with "straight" sidewalls 7. Because the sidewalls 7 are "straight," and generally vertical with respect to the lateral force 5 applied to the prosthesis 2, the resultant stress forces $f_i$ applied to adjacent bone 3 at any particular location along the length of one side 7 of the implant body 1 differ only from the stress forces $f_i$ applied to bone at another location by the distance between the location and the centroid 6 of the implant body 1. Thus, a force diagram similar to FIG. 2 will always result from lateral forces 5 applied to implant bodies 1 having "straight" sides 7.

Consider now the endosseous implant body 10 and prosthesis 12 illustrated in FIG. 4. Note that the implant body 10 of FIG. 4 does not have "straight" sides. Rather the sides 14 have surfaces 16 of two different types: (1) surfaces which generally face the coronal end 18 of the implant body 10, and (2) surfaces which generally face the distal end 20 of the implant body 10. It can be mathematically shown that the surfaces facing the coronal end 18 of the implant body 10 (which shall herein be referred to as "tension surfaces 22") generally exert less stress on bone 3 adjacent to the implant body 10 than do surfaces generally facing perpendicular to the implant body 10 (as in prior art implant bodies with "straight sides"). Also, it can be mathematically shown that the surfaces facing the base of the implant body (herein referred to as "compression surfaces 24") generally exert greater stress on bone 3 adjacent to the impact body 10 than do surfaces generally facing perpendicular to the implant body 10. Still further, it can be mathematically shown that between any two otherwise identical tension surfaces 22 or any two otherwise identical compression surfaces 24, the surface having the greater surface area and/or the surface having the greatest "angle of incidence 26" will exert the greater stress on bone 3 adjacent to the implant body 10. As illustrated in FIG. 4, the "angle of incidence 26" is herein defined as the obtuse angle resulting from the intersection of the longitudinal axis 28 of the implant body 10 and a line 30 disposed tangent to the particular surface 16 in question. FIG. 4 illustrates an implant body having two tension surfaces ($t_1$ and $t_2$, respectively) and two compression surfaces ($c_1$ and $c_2$, respectively). The angle of incidence of tension surface $t_1$ is $x_1$, and the angle of incidence of tension surface $t_2$ is $x_2$. Similarly, the angle of incidence of compression surface $c_1$ is $y_1$ and the angle of incidence of compression surface $c_2$ is $y_2$.

Based upon these properties of tension surfaces 22 and compression surfaces 24, the inventor has constructed an implant body 10 which substantially evenly distributes lateral stresses 5 placed upon the impact body 10 (such as illustrated in FIG. 3). The inventor has accomplished this by providing an implant body 10 having alternating tension surfaces 22 and compression surfaces 24. The surface areas and angles of incidence 26 of the tension surfaces 22 are chosen so that the portion of a lateral force 5 exerted by each of the tension surfaces increases from the centroid to the coronal end of the implant body. Conversely, the surface areas and angles of incidence of the compression surfaces 24 are chosen so that the portion of a lateral force 5 exerted by each of the compression surfaces 24 decreases from the centroid of the implant body to the coronal end of the implant body. Because the compression surfaces 24 exert more stress on adjacent bone 3 than do "straight surfaces," stress applied to bone 3 near the centroid 32 of the implant body of the invention 10 is greater than stress applied at the centroid 6 of prior art implant bodies 1. Conversely, because tension surfaces 22 exert less stress on adjacent bone 3 than do "straight surfaces," the stress applied to bone 3 near the coronal end 18 of the implant body of the invention 10 is less than stress applied to bone 3 near the coronal end of a prior art implant body 1. Thus, the stress diagram associated with the implant body of the invention more closely approximates FIG. 3 than FIG. 2.

Figure 6:
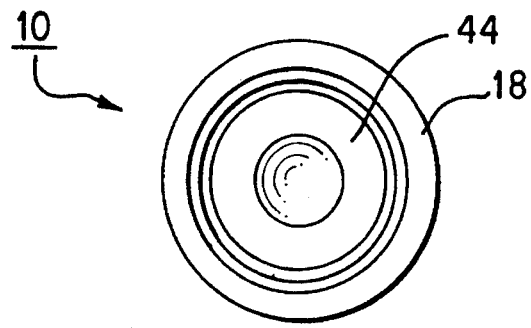
FIG. 6 is the coronal end view of the implant body shown in FIG. 5.
Figure 5:
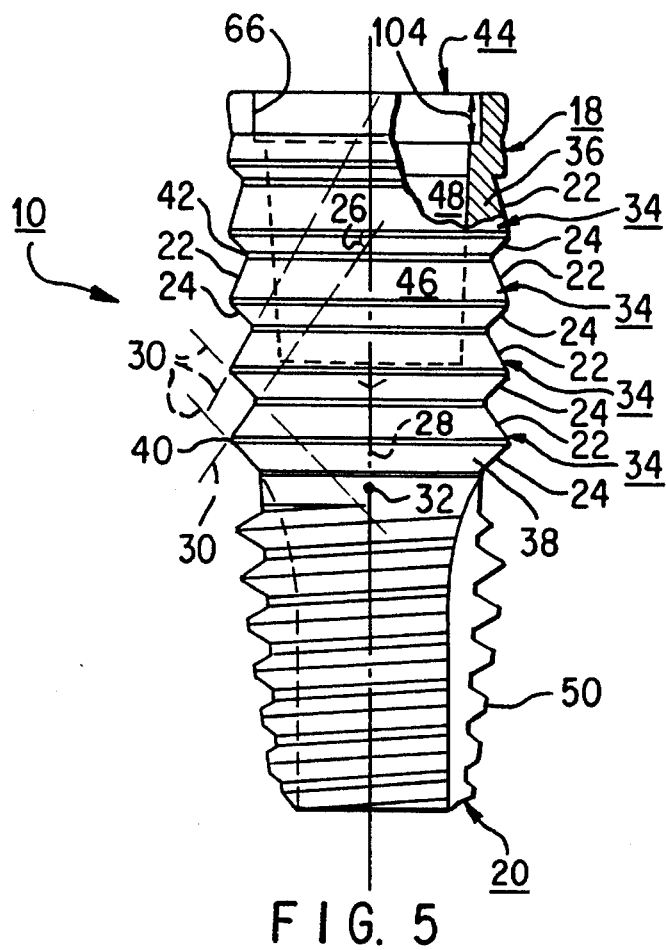
FIG. 5 is a side view of an implant body having features of the invention.
Figure 7:
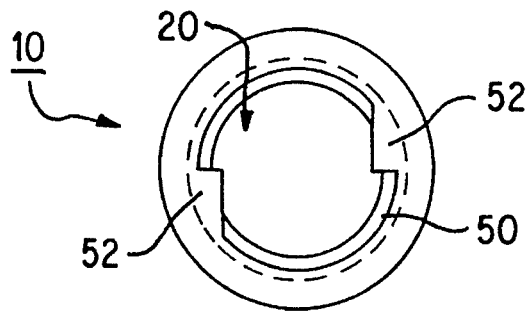
FIG. 7 is the distal end view of the implant body of FIG. 5.

A typical embodiment of the implant body 10 of the present invention is illustrated in FIGS. 5–7. The implant body 10 has a coronal end 18, a distal end 20, a longitudinal axis 28, and a plurality of segments 34 proximate to the coronal end 18.

Each segment 34 has a circular cross-section perpendicular to the longitudinal axis 28 and comprises a frustro-conical tension moiety 36 and a frustro-conical compression moiety 38. Both moieties 36 and 38 have a maximum diameter 40, a minimum diameter 42, and a substantially flat surface area 16 disposed therebetween. Each such surface 16 is disposed at an angle of incidence 26 with respect to the longitudinal axis 28. The maximum diameter 40 of the compression moiety 38 in each segment 34 is the same as the maximum diameter 40 of the tension moiety 36 in that segment 34. As can be seen in FIG. 5, each compression moiety 38 is joined to a tension moiety 36 along each moiety's respective maximum diameter 40. As can also be seen in FIG. 5, the minimum diameter 42 of each compression moiety 38 is identical to and is attached to the minimum diameter 42 of a tension moiety 36 of an adjacent segment 34.

As noted above, the angles of incidence 26 and the surface areas of the compression moieties 38 are chosen so that, when the implant body 10 is implanted into bone 3 and a lateral force 5 is applied to the coronal end 18 of the implant body 10, that portion of the lateral force 5 which is exerted by the compression moiety 38 of each segment 34 against the surrounding bone 3 is greater than that portion of the lateral force 5 which is exerted by the compression moiety 38 of an adjacent segment 34 disposed more proximate to the coronal end 18. Also, the angles of incidence 26 and the surface areas of the tension moieties 36 are chosen so that, when the implant body 10 is implanted into bone 3 and a lateral force 5 is applied to the coronal end 18 of the implant body 10, that portion of the lateral force 5 which is exerted by the tension moiety 36 of each segment 34 against the surrounding bone 3 is less than that portion of the lateral force 5 which is exerted by the tension moiety 36 of an adjacent segment 34 disposed more proximate to the coronal end 18.

In one typical embodiment of the implant body 10 of the invention, the vertical width 44 of each individual segment 34 is generally held constant and the width of each compression moiety surface 16 is made greater than the width of the compression moiety surface 16 of an adjacent segment 34 disposed more proximate to the distal end 20. In this embodiment, it is common, although not necessary, that the width of each tension moiety surface 16 is made greater than the width of the tension moiety surface 16 of an adjacent segment 34 disposed more proximate to the coronal end 18.

In another typical embodiment of the implant body 10 of the invention, the vertical width of each segment 34 is held generally constant and the angle of incidence 26 of each compression moiety surface 16 is greater than the angle of incidence 26 of the compression moiety 38 of an adjacent segment 34 disposed more proximate to the distal end 20. In this embodiment, it is common, although not necessary, that the angle of incidence 26 of each tension moiety surface 16 is greater than the angle of incidence 26 of the tension moiety surface 16 of an adjacent segment 34 disposed more proximate to the coronal end 18.

One of ordinary skill in the art will immediately recognize that the typical embodiments described immediately above are not necessarily the only applications of the invention. Any combination of angles of incidence 26 and surface areas can be combined in a series of segments 34 so long as, when the implant body 10 is implanted into bone 3 and a lateral force 5 is applied to the coronal end 18 of the implant body 10, (1) that portion of the lateral force 5 which is exerted by the compression moiety 38 of each segment 34 against the surrounding bone 3 is greater than the portion of the lateral force 5 which is exerted by the compression moiety 38 of an adjacent segment 34 disposed more proximate to the coronal end 18 and (2) that portion of the lateral force 5 which is exerted by the tension moiety 36 of each segment 34 against the surrounding bone 3 is less than that portion of the lateral force 5 which is exerted by the tension moiety 36 of an adjacent segment 34 disposed more proximate to the coronal end 18.

The segments 34 can be discrete, as illustrated in the drawings. Alternatively, the segments 34 can be disposed in one continuous helix.

Figure 8A:
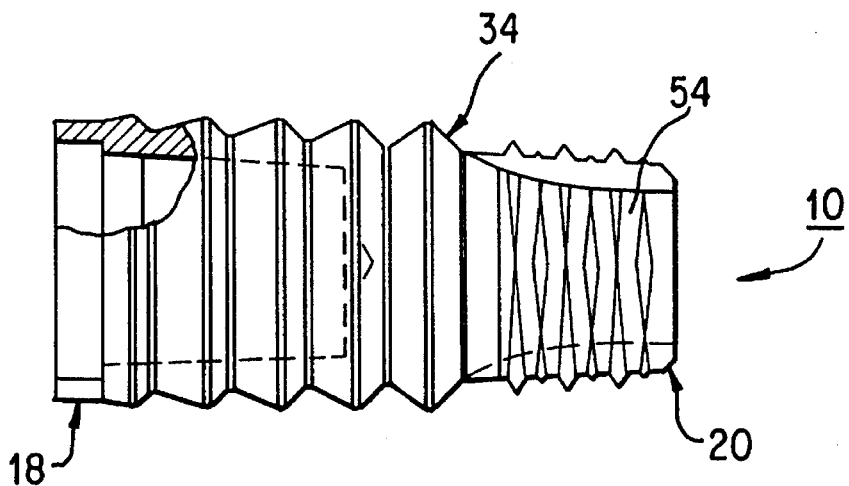
FIG. 8 is a side view of three implant bodies having features of the invention, including knurled distal ends.
Figure 8B:
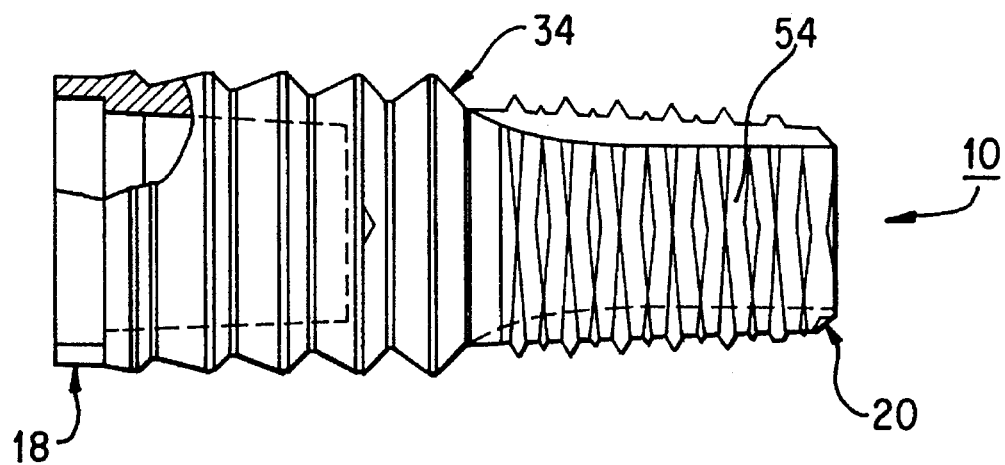
Figure 8C:
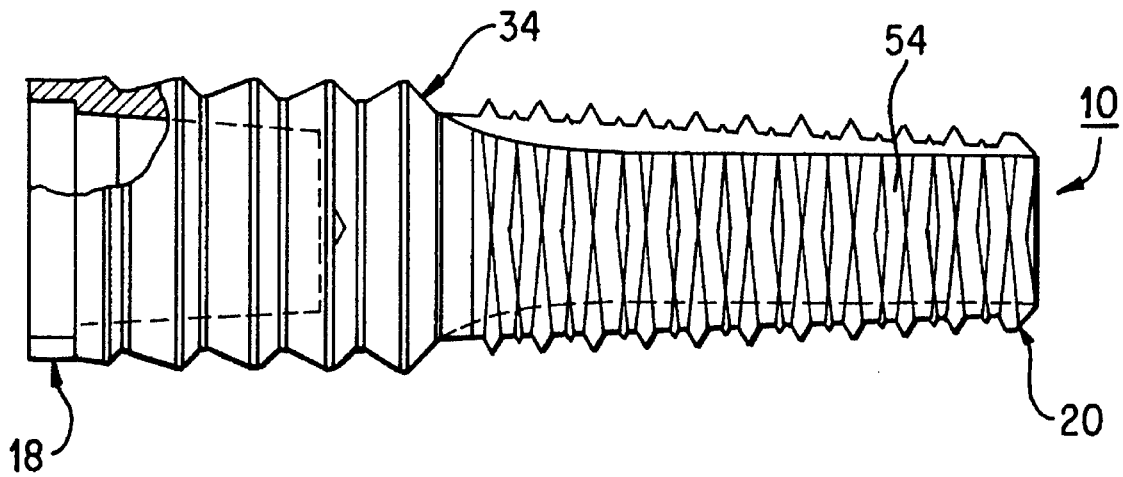

The implant body 10 is made from one of the many corrosion resistant metal alloys known in the art. For dental implants, the overall length of the implant body 10 is typically between about 8 millimeters and about 18 millimeters. FIG. 8 illustrated three different sizes of implant bodies 10.

A typical dental implant body of the invention 10 has four segments 34. The distance between the minimum diameter 42 of the compression segment 38 nearest the coronal end 18 of the implant body 10 and the minimum diameter 42 of the tension moiety 36 most distal to the coronal end 18 of the implant body 10 is typically between about 4 and about 8 millimeters. Implant bodies 10 having additional segments 34 are, of course, possible.

As can be seen from FIGS. 5 and 6, the coronal end 18 of the implant body 10 defines a tapered coronal bore 44 having circular cross-sections perpendicular to the longitudinal axis 28 of the implant body 10. The coronal bore 44 comprises a tapered distal section 46 and a coronal section 48. The coronal section 48 has a substantially circular cross-section which is greater than the maximum cross-section of the distal section 46. As will be seen below, the fact that the coronal section 48 has greater cross-section than the distal section 46 is important in that it allows for the attachment of a prosthesis attachment structure to be "countersunk" into the implant body 10, below the level of the bone crest.

In a typical embodiment, the distal end 20 of the implant body 10 is slightly tapered towards the distal end 20. Such tapering facilitates the firm installation of the implant body 10 into an implant site.

The distal end 20 of the implant body 10 can be externally threaded with self-tapping threads 50 as illustrated in FIG. 7. In this embodiment, it is preferred that a pair of grooves 52, disposed 180° apart, are defined within the exterior surface of the distal end 20. The grooves 52 provide space for bone chips to gather when the implant body 10 is threaded into the implant site.

Preferably, the distal end 20 of the implant body 10 is knurled as illustrated in FIG. 8. Most preferably, the distal end 20 of the implant body 10 is knurled and the knurling 54 has a cross-cut diamond shape, such as illustrated in FIG. 8. Such knurling 54 creates its own bone chips at the time of insertion which further assist in redistributing stresses placed on the implant body 10.

The implant body 10 is preferably used in conjunction with an anti-rotational plug 56 such as illustrated in FIGS. 9–12. The plug 56 acts as a host for all coronal attachments. The plug 56 has a distal moiety 58, a coronal moiety 60, and a longitudinal axis 62. The distal moiety 58 is sized and dimensioned to match the coronal bore 44 of the implant body 10 so that the plug 56 can be firmly affixed therein. The plug 56 may also be designed with parallel walls as shown in FIG. 9A to assure parallelism between the longitudinal axis 26 of the implant body 10 and the longitudinal axis of the plug 56 during assembly. In this case, a Mores taper would preferably be defined in the attachment structure (described below). The coronal moiety 60 of the plug 56 would be machined most preferably at a 2° Mores taper to assure accuracy and stability.

The coronal moiety 60 has a maximum cross-section perpendicular to the longitudinal axis 62 of the plug 56 which is smaller than the maximum cross-section of the distal moiety 58 perpendicular to the longitudinal axis 62 of the plug 56. As can be seen from FIG. 13 (which illustrates a typical plug 56 disposed within an implant 10), the fact that the coronal moiety 60 of the plug 56 has a smaller cross-section than the distal moiety 58, results in an annular gap 64 between the inner surface 66 of the coronal bore 44 within the implant body 10 and the coronal moiety 60 of the plug 56. As will be shown below, this annular gap 64 facilitates the "countersinking" of the prosthesis attachment structure (described below) to the implant body-plug combination 76. Alternatively, the tapered segment which creates the annular gap 64 may be defined in the prosthesis attachment structure in both the plug 56 and the prosthesis attachment structure to create an intimate fit upon proper seating.

The coronal moiety 60 of the plug 56 has at least one cross-section perpendicular to the longitudinal axis 62 of the plug which is non-circular. As will be seen below, this important feature allows for the reinstallation of an attachment structure (which has been previously removed from the coronal moiety 60 of the plug 56) to precisely the original location. The non-circular cross-section of the coronal moiety 60 can take on any of a wide variety of shapes. As shown in FIG. 10, the coronal moiety 60 of the plug 56 has a single cam projection 68. In the embodiment illustrated in FIG. 12, the coronal moiety 60 of the plug 56 has a hexagonal cross-section. Key-ways, locking splines, slots, flats and other cross-sectional shapes can also be used.

The coronal moiety 60 has an internally threaded plug bore 70 disposed along the longitudinal axis 62 of the plug 56. This threaded plug bore 70 facilitates the installation of a prosthesis 12 or other attachments to the plug 56 by providing an attachment site for an attachment screw.

Regardless of the shape of the coronal moiety 60 of the plug 56, it is preferred that the coronal moiety 60 be slightly tapered. It is most preferred that such tapering be a Mores taper 71 of between about 1° and about 2°, ideally, 1°, 30'. Such taper facilitates the installation of an attachment structure to the coronal moiety 60.

In practice, the plug 56 is disposed within the implant body 10 as illustrated in FIGS. 13–14. The plug 56 can be welded within the implant body 10, cemented, or attached by any other suitable means.

The distal end 58 of the plug 56 is slightly typically tapered as is the distal section 46 of the coronal bore 44 within the implant body 10. Such matched tapering facilitates the installation of the plug 56 within the implant body 10. Alternatively, the plug 56 is not tapered. This shape may be preferred to assure proper orientation of the plug 56 prior to welding within the implant body 10.

Figure 17:
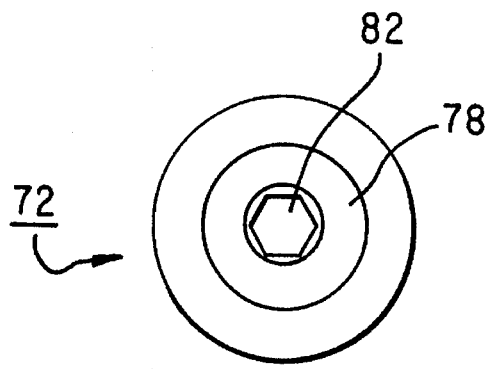
FIG. 17 is a coronal end view of the healing cap of FIG. 15.
Figure 19:
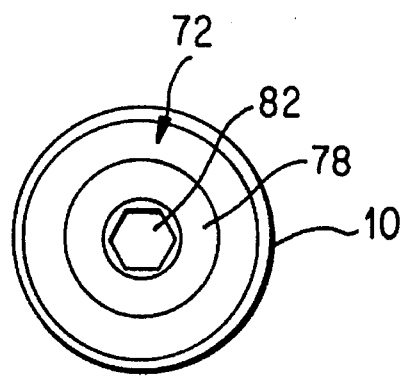
FIG. 19 is a coronal end view of the combination of FIG. 18.
Figure 15:
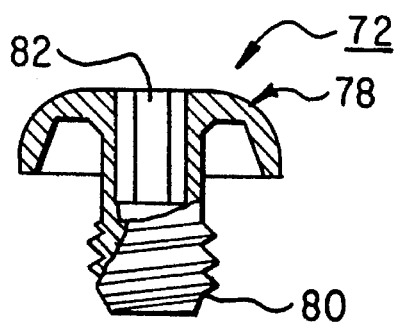
FIG. 15 is a side view in partial cross-section of a healing cap useful in the invention.
Figure 16:
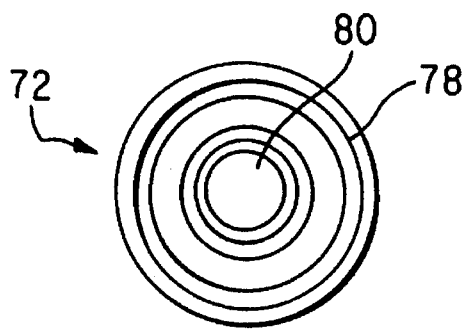
FIG. 16 is a distal end view of the healing cap of FIG. 15.
Figure 18:
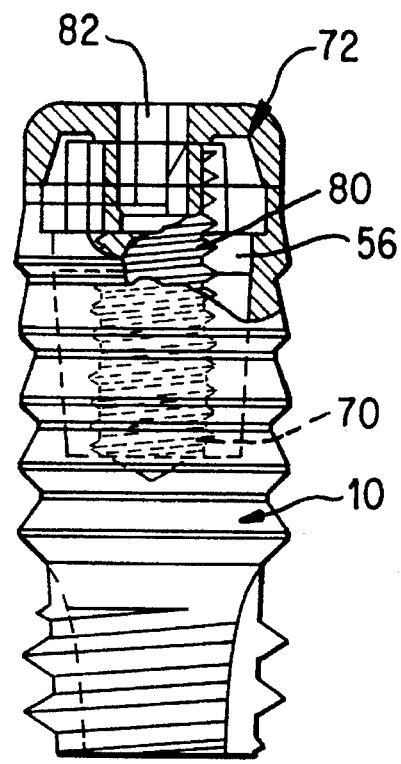
FIG. 18 is a side view in partial cross-section of the combination of an implant body-plug and healing cap having features of the invention.

FIGS. 15–17 illustrate a typical healing cap 72 useful in the invention. The healing cap 72 can be used to seal the coronal end 74 of the tapered implant body-plug combination 76 after the combination 76 has been implanted into a patient (as illustrated in FIGS. 18 and 19). The healing cap 72 has a cap portion 78 sized and dimensioned to match up with the coronal end 18 of the implant body 10. The healing cap 72 also has a threaded distal end 80 sized and dimensioned to thread into the internally threaded plug bore 70 of the plug 56. The cap portion 78 has a coronal bore 82 with a non-circular cross-section. This bore 82 is adapted to accept a torquing tool which can be used to thread the healing cap 72 into the coronal moiety 60 of the plug 56.

FIGS. 20–21 illustrate a typical attachment structure 84 useful for attaching impression attachments, prostheses or other attachments to the implant body-plug combination 67. The attachment structure 84 comprises an elongated hollow section 86 having a coronal moiety 88 with an open coronal end 90, a distal moiety 92 with an open distal end 94 and a longitudinal axis 96. The distal end 94 of the attachment structure 84 is shaped and dimensioned to receive and engage the non-circular cross-section of the coronal moiety 60 of the plug 56. In the embodiment shown in the drawings, the distal end 94 of the attachment structure 84 is shaped to receive the coronal end 60 of a plug 56 having a cam projection 68, such as illustrated in FIG. 9. As mentioned above, this feature allows the practitioner to remove the attachment structure 84 from the plug 56 and thereafter reinstall the attachment structure 84 onto the plug 56 in precisely the same alignment in which it was initially installed. Alternatively, one or both components may also be machined parallel and alone be tapered to achieve the same results. The coronal moiety 88 is preferably detachable from the distal moiety 92.

The attachment structure 84 can be affixed to the plug 56 by an elongated first screw 98 which is disposed within the hollow section 86 of the attachment structure 84. Such a first screw 98 is illustrated in FIGS. 22 and 23. The threads of the first screw 98 are chosen to match the internal threads in the bore 70 of the plug 56. FIG. 24 illustrates the first screw 98 disposed within the attachment structure 84. The first screw 98 has a coronal bore 99 with a non-circular cross-section. This bore 99 is adapted to accept a torquing tool which can be used to thread the first screw 98 into the coronal moiety 60 of the plug 56.

Figure 25:
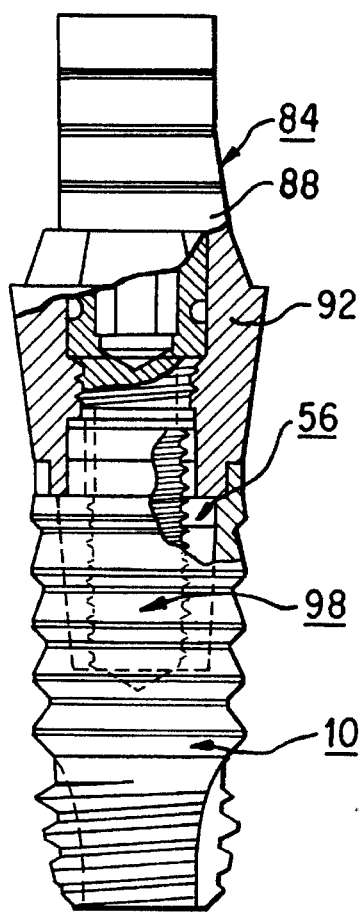
FIG. 25 is a side view in partial cross-section of another implant combination having features of the invention.

In the embodiments illustrated in the drawings, the distal moiety 92 of the attachment structure 84 has a first external surface section 100 immediately proximate to the distal end 94 of the attachment structure 84 and a second external surface section 102 immediately proximate to the first external surface section 100. The cross-sections of the first and second external surface sections 100 and 102 are sized and dimensioned to match the cross-section of the external surface of the implant body 10 immediately proximate to the coronal end 18 of the implant body 10. The width 103 of the first external surface section 100 is substantially the same as the depth 104 of the coronal section 48 of the implant body coronal bore 44. As shown in FIG. 25, this design allows the first external surface section 100 to nest within the coronal section 18 of the coronal bore 44 of the implant body 10. The diameter of the second external surface section 102 is substantially the same as the diameter of the external surface of the implant body 10 immediately proximate to its coronal end 18. As illustrated in FIG. 25, this provides for a smooth transitional surface between the impact body 10 and the attachment structure 84.

Figure 26:
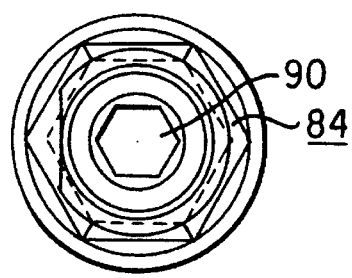
FIG. 26 is a coronal end view of the combination of FIG. 20.
Figure 27:
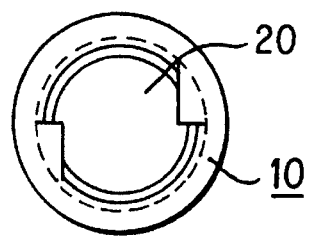
FIG. 27 is a distal end view of the combination of FIG. 20.

FIGS. 25–27 illustrate the attachment structure 84 as it is combined with the implant body 10 and the plug 56, using the first screw 98.

Figure 28:
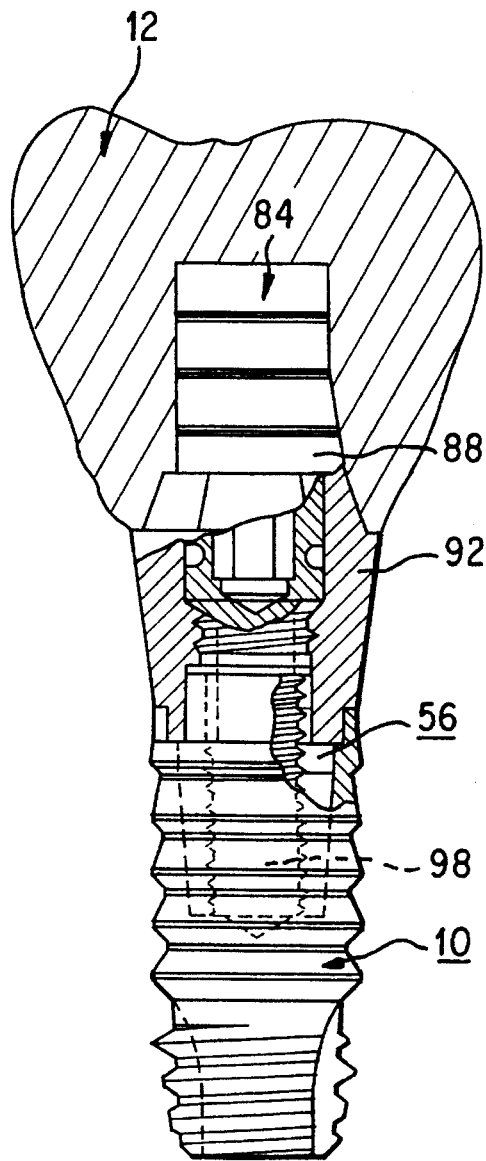
FIG. 28 is a side view in partial cross-section of a further combination having features of the invention.
Figure 41:
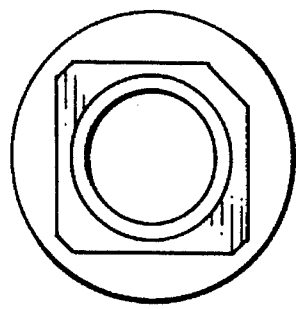
FIG. 41 is a coronal end view of the shank of FIG. 39.
Figure 44:
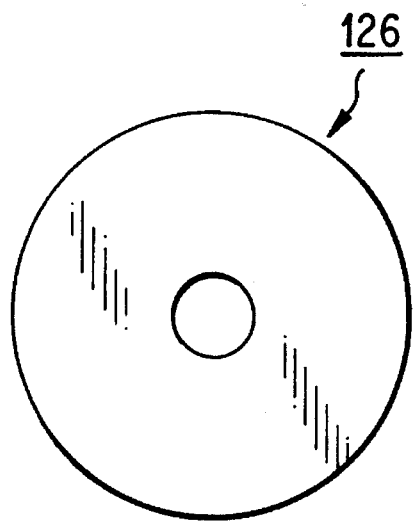
FIG. 44 is a coronal end view of the handle of FIG. 42.
Figure 39:
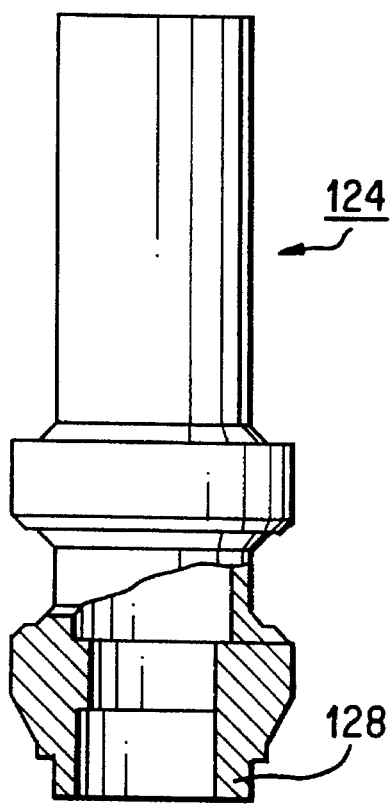
FIG. 39 is a side view in partial cross-section of a tool shank useful in the delivery system of FIG. 36.
Figure 42:
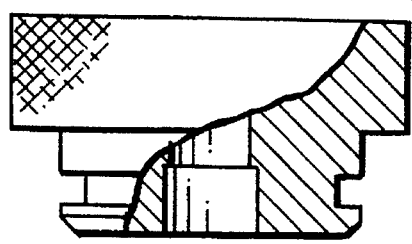
FIG. 42 is a tool handle useful in the delivery system of FIG. 36.
Figure 40:
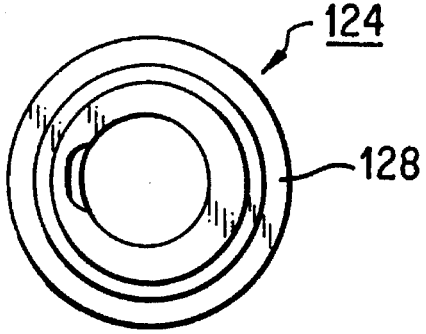
FIG. 40 is a distal end view of the tool shank of FIG. 39.
Figure 43:
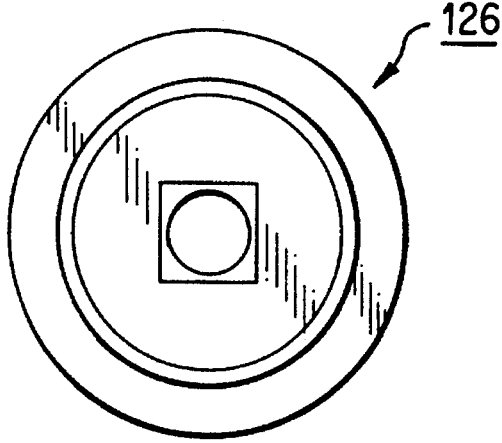
FIG. 43 is a distal end view of the handle of FIG. 42.
Figure 46:
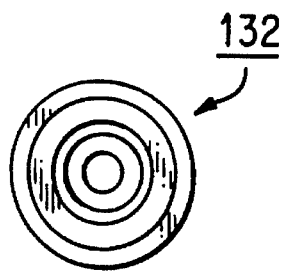
FIG. 46 is a coronal end view of the pilot drill of FIG. 45.
Figure 49:
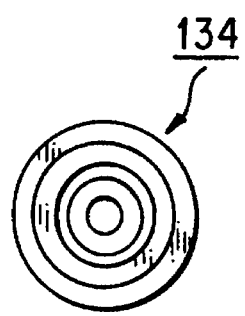
FIG. 49 is a coronal end view of the drill of FIG. 48.

FIG. 28 illustrates the combination illustrated in FIG. 25 in further combination with a dental prosthesis 12 attached to the attachment structure 84.

In many cases prior to the final installation of the prosthesis 12 onto the attachment structure 84, it is desirable to cover the attachment structure 84 with a sheath 106. Such a sheath 106 is illustrated in FIGS. 31–33. As shown in FIG. 31, to install the sheath 106, the practitioner first removes the coronal moiety 88 of the attachment structure 84. The sheath 106 can be made of a plastic material. Other suitable materials can, of course, be used, i.e., $T_i$, $T_i$ 6-4 alloy or $T_i$ 13—13, etc.

The sheath 106 has an open coronal end 108 and an open distal end 110. The coronal end 108 is sized and dimensioned to cover the coronal end 90 of the attachment structure 84. The opening 112 in the coronal end 108 of the sheath 106 is sized and dimensioned to receive a second screw 114 as illustrated in FIGS. 34 and 35. The second screw 114 is threaded in such a way that it can be attached within the bore 70 of the plug 56. The second screw 114 has a shoulder 116 sized and dimensioned to firmly retain the attachment structure 84 to the plug 56. The second screw 114 also has a head 118 sized and dimensioned to firmly attach the sheath 106 to the attachment structure 84. The second screw 114 has a coronal bore 119 with a non-circular cross-section. This bore 119 is adapted to accept a torquing tool which can be used to thread the second screw 114 into the coronal moiety 60 of the plug 56.

As illustrated in FIG. 36, the implant body-plug combination 76 can be conveniently packaged with an implant tool 120 within a protective cover 122 so that the practitioner can quickly and easily install the implant body-plug combination 76 by merely removing the cover 122 and using the installation tool 120 to install the implant body 10 within a pre-prepared implant site. A typical implant tool 120 is illustrated in FIGS. 37–44.

The tool 120 comprises a shank portion 124 which is attachable to a removable handle portion 126. The distal end 128 of the shank portion 124 is sized and dimensioned to match up and engage the coronal moiety 60 of the plug 56 and the coronal end 18 of the implant body 10. The distal end 128 of the shank 124 is sized and dimensioned to accept the removable handle portion 126. Both the handle portion 126 and the shank 124 are hollow so that a third screw 130 can be used to firmly attach the handle portion 126 to the shank 124 and the shank 124 to the plug 56 as illustrated in FIG. 36. The third screw 130 has a coronal bore 131 with a non-circular cross-section. This bore 131 is adapted to accept a torquing tool which can be used to thread the third screw 130 into the coronal moiety 60 of the plug 56.

Figure 45:
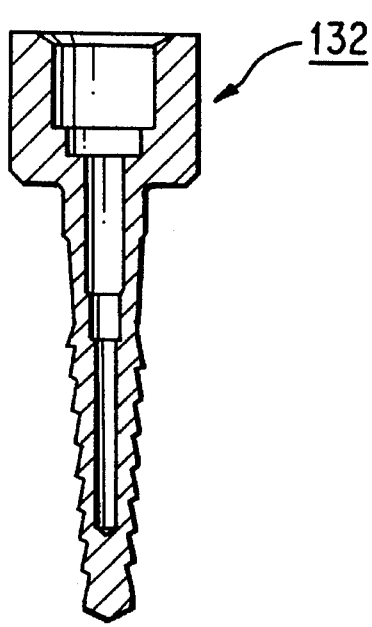
FIG. 45 is a side view in partial cross-section of a pilot drill useful in the invention.
Figure 48:
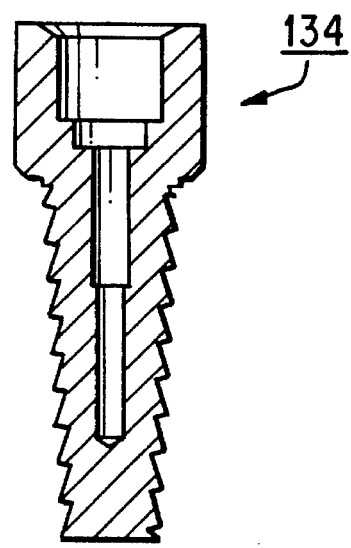
FIG. 48 is a side view in partial cross-section of a drill useful in the invention as the final sizing drill prior to insertion.
Figure 47:
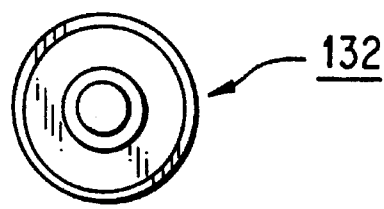
FIG. 47 is a distal end view of the pilot drill of FIG. 45.
Figure 50:
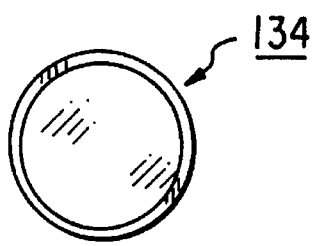
FIG. 50 is a distal end view of the drill of FIG. 48.

In practice, the implant body of the invention 10 is installed into an implant site which has been previously prepared in the bone 3 of the patient. Such an implant site can be prepared using tapered drills such as those illustrated in FIGS. 45–50. The drill illustrated in FIG. 45 is a typical pilot drill 132. The drill illustrated in FIG. 48 is a larger drill 134 for use after a pilot hole is drilled (by the pilot 132 drill) to prepare the full dimension of the implant site.

Although the present invention has been described in considerable detail with reference to certain preferred versions, many other versions should be apparent to those skilled in the art. Therefore, the spirit and scope of the appending claims should not necessarily be limited to the description of the preferred versions contained herein.

What is claimed is:

1. An endosseous implant body for implantation into bone, the body having a coronal end, a distal end, a longitudinal axis and a plurality of segments proximate to the coronal end, wherein:

(a) each segment has a circular cross-section perpendicular to the longitudinal axis and comprises a frustro-conical compression moiety and a frustro-conical tension moiety, both moieties have a maximum diameter, a minimum diameter and a substantially flat surface area disposed therebetween at an angle of incidence with respect to the longitudinal axis, the maximum diameter of the compression moiety being the same as the maximum diameter of the tension moiety and the compression moiety being joined to the tension moiety along each moiety's respective maximum diameter;

(b) the minimum diameter of each compression moiety is identical to and is attached to the minimum diameter of a tension moiety of an adjacent segment;

(c) the angles of incidence and the surface areas of the compression moieties are chosen so that, when the implant body is implanted into bone and a lateral force is applied to the coronal end of the implant body, that portion of the lateral force which is exerted by the compression moiety of each segment against the surrounding bone is greater than that portion of the lateral force which is exerted by the compression moiety of an adjacent segment disposed more proximate to the coronal end; and (d) the angles of incidence and the surface areas of the tension moieties are chosen so that when the implant body is implanted into bone and a lateral force is applied to the coronal end of the implant body, that portion of the lateral force which is exerted by the tension moiety of each segment against the surrounding bone is less than that portion of the lateral force which is exerted by the tension moiety of an adjacent segment disposed more proximate to the coronal end.

2. The implant body of claim 1 having at least four segments and wherein the distance between the minimum diameter of the compression segment nearest the coronal end and the minimum diameter of the tension moiety most distal from the coronal end is between about 4 and about 8 millimeters.

3. The implant body of claim 1 wherein the distance between the coronal end and the distal end is between about 8 and about 18 millimeters.

4. The implant body of claim 1 wherein the width of each compression moiety surface between the minimum diameter of the compression moiety and the maximum diameter of the compression moiety is greater than the width of the compression moiety surface between the minimum diameter of the compression moiety and the maximum diameter of the compression moiety of an adjacent segment disposed more proximate to the distal end.

5. The implant body of claim 1 wherein the width of each tension moiety surface between the minimum diameter of the tension moiety and the maximum diameter of the tension moiety is greater than the width of the tension moiety surface between the minimum diameter of the tension moiety and the maximum diameter of the tension moiety of an adjacent segment disposed more proximate to the coronal end.

6. The implant body of claim 1 wherein the angle of incidence of each compression moiety surface between the minimum diameter of the compression moiety and the maximum diameter of the compression moiety is greater than the angle of incidence of the compression moiety surface between the minimum diameter of the compression moiety and the maximum diameter of the compression moiety of an adjacent segment disposed more proximate to the distal end.

7. The implant body of claim 1 wherein the angle of incidence of each tension moiety surface between the minimum diameter of the tension moiety and the maximum diameter of the tension moiety is greater than the angle of incidence of the tension moiety surface between the minimum diameter of the tension moiety and the maximum diameter of the tension moiety of the tension moiety of an adjacent segment disposed more proximate to the coronal end.

8. The implant body of claim 1 wherein the coronal end defines a tapered coronal bore having circular cross-sections perpendicular to the longitudinal axis, and wherein the coronal bore comprises a tapered distal section and a coronal section, the coronal section having a substantially circular cross-section which is greater than the maximum cross-section of the distal section.

9. The implant body of claim 1 wherein the exterior surface proximate to the distal end is externally threaded.

10. The implant body of claim 1 wherein the exterior surface proximate to the distal end is externally knurled.

11. An endosseous implant combination comprising:

(a) an implant body having a distal end, a coronal end and a longitudinal axis, the coronal end defining a tapered coronal bore having circular cross-sections perpendicular to the longitudinal axis; and (b) a plug having a plug distal moiety, a plug coronal moiety and a longitudinal axis, the plug distal moiety being sized and dimensioned to match the coronal bore of the implant body and being affixed therein, the plug coronal moiety having a maximum cross-section perpendicular to the longitudinal axis which is smaller than the maximum cross-section of the plug distal moiety perpendicular to the longitudinal axis and less than a maximum cross-section of a portion of said coronal bore of said implant body for forming an annular gap therebetween for installation of an attachment structure therein, the plug coronal moiety having at least one cross-section perpendicular to the longitudinal axis which is non-circular and the plug coronal moiety defining an internally threaded plug bore disposed along the longitudinal axis of the plug.

12. The combination of claim 11 wherein the coronal moiety of the plug is tapered to a Mores taper of between about one degree and about two degrees.

13. The combination of claim 12 wherein the coronal moiety of the plug has at least one cross-section which is substantially hexagonal.

14. The combination of claim 11, wherein the distal moiety of the plug is tapered.

15. The combination of claim 11 wherein the implant body coronal bore has a distal section and a coronal section, the distal section being tapered and having a maximum cross-sectional diameter which is less than the cross-sectional diameter of the coronal section and wherein the plug is disposed within the distal section of the implant body coronal bore.

16. The combination of claim 11 further comprising an attachment structure, the attachment structure comprising an elongated hollow section having a coronal moiety with an open coronal end, a distal moiety with an open distal end and a longitudinal axis, the distal end of the attachment structure being shaped and dimensioned to receive and engage the non-circular cross-section of the coronal moiety of the plug, the attachment structure being affixed to the plug by an elongated screw disposed within the hollow section, the screw having a head and an externally threaded end, the threaded end being threaded into the plug bore, whereby the head of the screw is accessed for applying torque to the screw through the open proximal end of the attachment structure.

17. The combination of claim 16 wherein:

(a) the implant body coronal bore has a distal section and a coronal section, the distal section being tapered and having a maximum cross-sectional diameter which is less than the cross-sectional diameter of the coronal section;

(b) the distal moiety of the attachment structure has a first external surface section immediately proximate to the distal end of the attachment structure and a second external surface section immediately proximate to the first external surface section;

(c) the cross-sections of the first and second external surface sections are substantially circular as is the cross-section of the external surface of the implant body immediately proximate to the coronal end;

(d) the diameter of the first external surface section is substantially the same as the cross-sectional diameter of the coronal section of the implant body coronal bore and the diameter of the second external surface section is substantially the same as the external diameter of the external surface of the implant body immediately proximate to the coronal end; and (e) the width of the first external surface section is substantially the same as the depth of the coronal section of the implant body coronal bore.

18. The combination of claim 16 further comprising a sheath for securely covering the open coronal end of the attachment structure, the sheath having a hollow body with an open distal end and an open proximal end, the open distal end being sized and dimensioned to conform to the proximal end of the attachment structure so that the sheath securely engages the coronal end of the attachment structure, the sheath being attached to the attachment structure by a screw engaged into the threaded plug bore, the screw having a head and an externally threaded end, the threaded end being threaded into the threaded plug bore and the head of the screw being accessed for applying torque to the screw through the open coronal end of the attachment structure.

19. The combination of claim 16 further comprising a dental prosthesis attached to the proximal end of the attachment structure.

20. The combination of claim 11 further comprising a healing cap having a threaded distal end and a coronal head, the threaded distal end being adapted to thread within the plug bore and the coronal head being sized and dimensioned to cover the coronal end of the implant body, the healing cap further comprising a coronal bore disposed coaxially with the longitudinal axis of the implant body and having a non-circular interior cross-section.

21. An endosseous implant delivery system combination comprising:

(a) an implant body having a distal end, a coronal end and a longitudinal axis, the coronal end defining a tapered coronal bore having circular cross-sections perpendicular to the longitudinal axis;

(b) a plug having a distal moiety, a coronal moiety and a longitudinal axis, the distal moiety being sized and dimensioned to match the coronal bore of the implant body and being affixed therein, the coronal moiety having a maximum cross-section perpendicular to the longitudinal axis which is smaller than the maximum cross-section of the distal moiety perpendicular to the longitudinal axis and less than a maximum cross-section of a portion of said coronal bore of said implant body for forming an annular gap therebetween, the coronal moiety having at least one cross-section perpendicular to the longitudinal axis which is non-circular and the coronal moiety defining a threaded plug bore disposed along the longitudinal axis of the plug; and (c) an elongated hollow wrench having a hollow body, an open proximal end and an open distal end, the distal end being shaped for insert into said gap and dimensioned to receive and engage the non-circular cross-section of the coronal moiety of the plug, the wrench being attached to the plug by an elongated screw disposed within the hollow body of the wrench, the screw having a head and an externally threaded end, the threaded end being threaded into the plug bore, whereby the head of the screw is accessed for applying torque to the screw through the open proximal end of the wrench.

* * * * *